United States Patent
Priev et al.

(10) Patent No.: US 7,484,414 B2
(45) Date of Patent: Feb. 3, 2009

(54) METHOD AND APPARATUS FOR DETERMINATION OF THE CONCENTRATION OF PARTICLES IN MULTI-COMPONENT FLUID SYSTEMS

(75) Inventors: Aba Priev, Maale Adumim (IL); Viktor Petrovich Ponomarev, Rostov-on-Don (RU)

(73) Assignee: NanoAlert Ltd., Maale Adumim (IL)

( * ) Notice: Subject to any disclaimer, the term of this patent is extended or adjusted under 35 U.S.C. 154(b) by 280 days.

(21) Appl. No.: 11/289,628

(22) Filed: Nov. 30, 2005

(65) Prior Publication Data
US 2007/0119239 A1 May 31, 2007

(51) Int. Cl.
G01N 29/00 (2006.01)
B01D 17/00 (2006.01)

(52) U.S. Cl. .................. 73/649; 73/24.06; 73/64.53; 73/571; 210/748

(58) Field of Classification Search ............. 73/649, 73/579, 571, 647, 19.03, 24.01, 24.06, 31.05, 73/61.45, 61.49, 64.53; 210/708, 748
See application file for complete search history.

(56) References Cited

U.S. PATENT DOCUMENTS

| | | | | |
|---|---|---|---|---|
| 4,743,361 A * | 5/1988 | Schram | ................... | 209/1 |
| 5,533,402 A | 7/1996 | Sarvazyan et al. | | |
| 5,626,767 A * | 5/1997 | Trampler et al. | ............ | 210/748 |
| 5,706,815 A * | 1/1998 | Sarvazyan et al. | .......... | 600/438 |
| 5,902,489 A * | 5/1999 | Yasuda et al. | ................ | 210/748 |
| 6,481,268 B1 * | 11/2002 | Povey et al. | ................ | 73/61.75 |
| 6,644,118 B2 * | 11/2003 | Kaduchak et al. | .......... | 73/570.5 |
| 6,796,195 B2 * | 9/2004 | Povey et al. | ................ | 73/865.5 |
| 6,881,314 B1 * | 4/2005 | Wang et al. | ................. | 204/600 |
| 6,916,113 B2 * | 7/2005 | Van de Goor et al. | ....... | 366/108 |
| 6,920,399 B2 | 7/2005 | Priev et al. | | |
| 6,929,750 B2 * | 8/2005 | Laurell et al. | ................ | 210/708 |
| 6,938,995 B2 * | 9/2005 | Mutz et al. | .................... | 347/75 |
| 7,270,001 B2 * | 9/2007 | Betz | ........................ | 73/290 V |
| 2006/0032935 A1 * | 2/2006 | Matsuura | ........................ | 239/9 |
| 2007/0295595 A1 * | 12/2007 | Matsuura | ................. | 204/158.2 |

* cited by examiner

*Primary Examiner*—Hezron E. Williams
*Assistant Examiner*—Jacques M. Saint-Surin
(74) *Attorney, Agent, or Firm*—Stites & Harbison PLLC; Ross F. Hunt, Jr.

(57) ABSTRACT

A method for determining the concentration of a large particle component in a multi-component system. The method requires first separating and concentrating the large particle component of the system by acoustic means and then measuring an acoustical parameter of the separated large particle component. The invention also provides for an apparatus for determining the concentration of large particles in a multi-component fluid system. The apparatus is comprised of an acoustic standing wave resonator, at least one acoustic standing wave generating source, electronic circuitry for actuating, controlling and processing the acoustic standing wave generating source and means for measuring at least one parameter of the multi-component system after the large particles have been concentrated and aggregated by the generated standing wave(s).

24 Claims, 11 Drawing Sheets

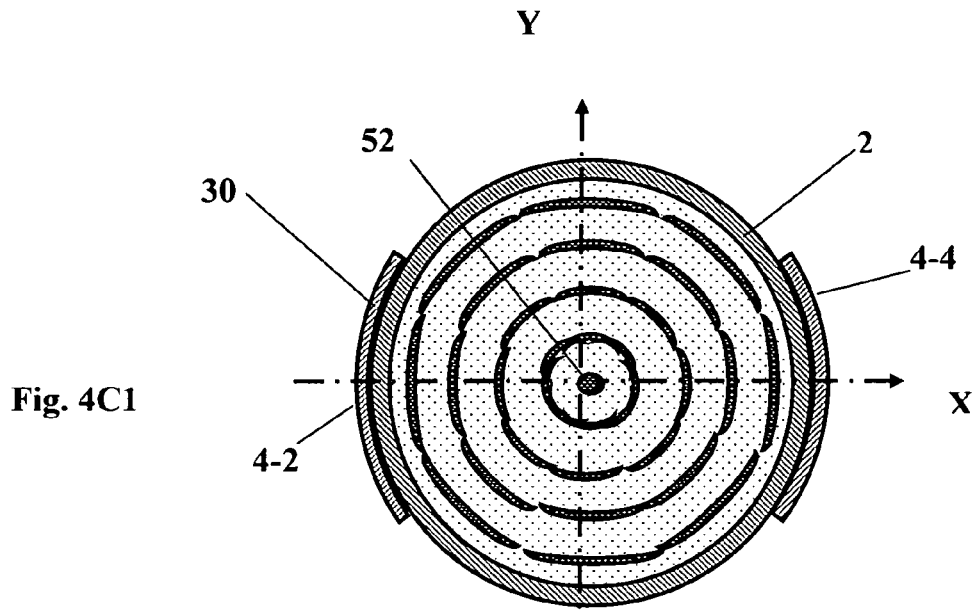
Fig. 4C1
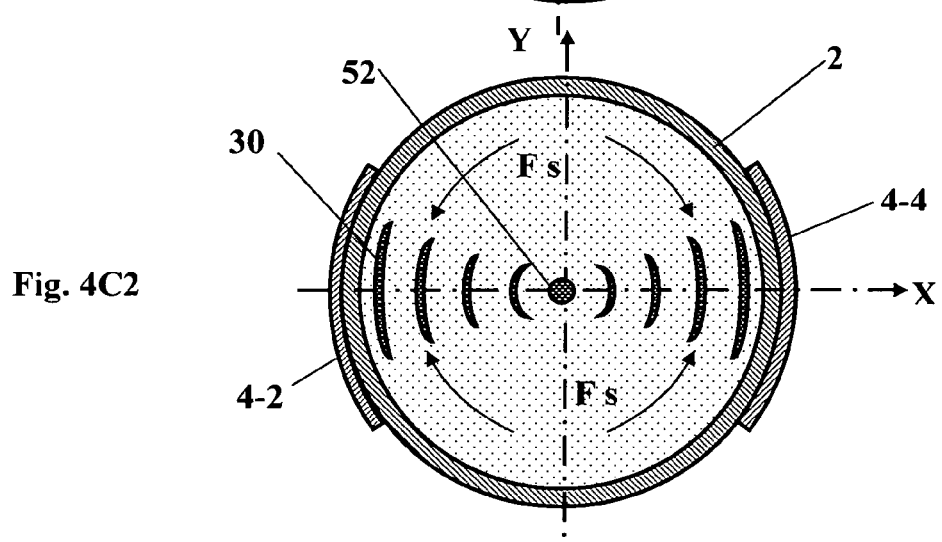
Fig. 4C2
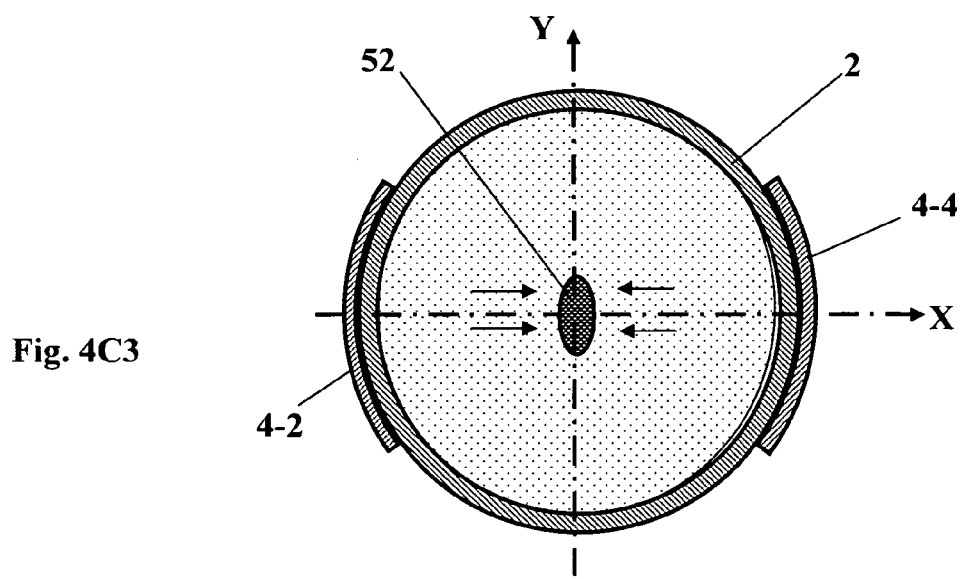
Fig. 4C3

METHOD AND APPARATUS FOR DETERMINATION OF THE CONCENTRATION OF PARTICLES IN MULTI-COMPONENT FLUID SYSTEMS

FIELD OF THE INVENTION

The present invention relates to a method and apparatus for determining the concentration of large particles in multi-component fluid systems.

BACKGROUND OF THE INVENTION

There are many applications for which it is necessary to measure the concentration of a component or components in a multi-component fluid system. Foods which are complex multi-component systems often need to have their constituents analyzed. A typical foodstuff for which its components need regular analysis is milk. Milk contains globules of butterfat, as well as somatic cells, proteins, lactose, and mineral salts dispersed as an aqueous emulsion. Various methods for analyzing foodstuffs are used. Spectroscopy, electrical conductivity and classical "wet chemistry" analytical methods are, or have been, employed in the past.

Over the last decade there has been increased interest in the use of ultrasound in characterizing the constituents of foods as well as other multi-component systems. Systems which have been analyzed by ultrasound techniques include solutions, suspensions and emulsions. Ultrasound has major advantages over many other analytical methods because it is nondestructive, rapid, relatively inexpensive, and can be applied to concentrated and/or optically opaque samples.

Ultrasound techniques use high-frequency sound waves, those in the upper kilohertz and megahertz frequency range, which are propagated through the material being tested. Information about the properties of the material is obtained by measuring the interaction between the propagated sound wave and the material.

It is known that the natural resonance frequencies of a liquid-containing acoustic resonator are linearly related to the velocity of ultrasound waves. In general, once a standing wave is obtained, one changes the applied frequency and monitors the wave's amplitude and phase at a detecting transducer as a function of applied frequency. This information facilitates calculation of the velocity and attenuation of the sound waves in the liquid. These parameters are related to, and can provide information about, the characteristics of the liquid, including the concentration of its constituents.

Prior art discusses using cylindrical standing wave ultrasonic resonators to determine the concentration of components in multi-component systems, such as milk, by measuring changes in ultrasonic acoustic properties. However, the methods and apparatuses discussed in prior art have drawbacks. For example, prior art methods require a second resonator to measure a reference sample. They also include measurements of the liquid's acoustic properties at different temperatures-and therefore require waiting for temperature equilibration of the sample when the sample is heated or cooled. In many ultrasound measurements of multi-component systems, flow-through samples can not be measured. Additionally, in prior art systems, ultrasonic methods generally only determine the concentration of small, dissolved species in multi-component systems, that is species present at concentrations greater than 0.01%. The concentration of larger particles, for example somatic cells or microbes in milk which are present at concentrations of less than 0.01%, cannot be determined. Furthermore, prior art systems can determine only a limited number of components typically up to about five components. The number of components is limited because the number of acoustic parameters which is measurable is limited.

SUMMARY OF THE PRESENT INVENTION

It is an object of the present invention to provide an apparatus and a method for determining the concentration of large particles in a multi-component fluid system.

It is a further object of the present invention to provide an apparatus and a method for ultrasonic determination of the concentration of large particles in a multi-component fluid system which is rapid and requires relatively low precision temperature control.

It is yet another object of the present invention to provide an apparatus and a method for ultrasound determination of the concentration of large particles in a multi-component fluid system based on the anisotropic particle distribution produced in the measuring chamber by the apparatus. This obviates the requirement for separate reference measurements.

It is yet another object of the present invention to provide an apparatus and method for the ultrasound determination of large particles in a multi-component fluid system using flow-through samples.

It is a further object of the present invention to allow measurement of a larger number of components in a system than prior art apparatuses and methods.

There is thus provided in accordance with one aspect of the present invention a method for determining the concentration of a large particle component in a multi-component system. The method includes the steps of: separating and concentrating by acoustic means the large particle component of the system, wherein the acoustic means generates at least one cylindrical standing wave in an acoustic cylindrical standing wave resonator; and measuring at least one acoustical parameter of the separated large particle component, thereby allowing determination of its concentration.

In some embodiments of the method, the at least one cylindrical standing wave is at least two cylindrical standing waves, each wave having a different frequency and intensity. In other embodiments, the at least one cylindrical standing wave is at least two cylindrical standing waves, each wave having a different frequency but all the waves having equal intensity. The large particles forming the large particle component being separated by the method has a particle size within the range of from about 50 nanometers to about 500 microns.

In one embodiment of the method, the step of measuring at least one acoustical parameter further includes the step of measuring at least one optical parameter. The optical parameter is selected from a group of optical parameters consisting of optical absorbance, fluorescence, and reflectance. In some instances, the optical parameter being measured in the step of measuring at least one optical parameter further includes the step of measuring the anisotropies of the at least one optical parameter.

In another embodiment of the method, at least one acoustical parameter is measured in the step of measuring. The at least one acoustical parameter is selected from a group of acoustical parameters consisting of acoustic wave velocity, acoustic wave attenuation, and acoustic impedance. In this embodiment, the at least one acoustical parameter is measured in two directions, the directions being perpendicular to each other, with the measurement in one direction representing a reference measurement.

Further, in accordance with an embodiment of the method of the present invention, the at least one acoustical parameter in the step of measuring is measured at one or more low acoustic intensities ranging between about 0.01 to about 1 W/cm², while separation and concentration of the large particles in the step of separating is effected at high acoustic intensities ranging between about 1 to about 30 W/cm². In an instance of this embodiment, in the step of measuring, a reference measurement is effected at a low acoustic intensity of about 0.01 to less than about 0.5 W/cm² and a sample measurement is effected at a low acoustic intensity of 0.5 to about 1 W/cm².

The method of the present invention further comprises the step of comparing the measured value of the at least one acoustical parameter to values calibrated as a function of concentration.

There is provided in another aspect of the present invention an apparatus for determining the concentration of large particles in a multi-component fluid system. The apparatus includes an acoustic standing wave manipulating device. The manipulating device includes a cylindrical acoustic standing wave resonator for containing a sample of the system and at least one acoustic standing wave generating source disposed adjacent to and acoustically coupled to the resonator. The at least one generating source generates at least one acoustic standing wave for concentrating and aggregating the large particles at at least one nodal region of the at least one standing wave. The cylindrical standing wave resonator includes at least one circumferential non-interference band near at least one end of the at least one acoustic standing wave generating source. The apparatus further includes electronic circuitry for actuating and controlling the at least one acoustic standing wave generating source and the frequencies and acoustical intensities generated by the source. The apparatus additionally includes means for measuring at least one parameter of the sample after the large particles have been concentrated and aggregated by the at least one standing wave.

In one embodiment of the apparatus each of the at least one non-interference bands is a circumferential bulge integrally formed in the walls of the cylindrical resonator or a circumferential constriction integrally formed in the walls of the cylindrical resonator. In other embodiments, the cylindrical standing wave resonator is formed with a circumferential non-interference band near each end of each of the acoustic standing wave generating sources.

In another embodiment of the apparatus, the at least one acoustic resonator is a plurality of acoustic resonators in fluid communication with each other, each resonator acoustically coupled to a different acoustic standing wave generating source, and each resonator having at least one non-interference band at each end of each of its generating sources. In some instances, the plurality of acoustic resonators includes resonators of different volumes.

In yet another embodiment of the apparatus, the means for measuring is an acoustic means operative to measure at least one acoustical parameter, where the acoustic means is at least one piezoelectric transducer element. In some instances of this embodiment, the means for measuring is an acoustic means and the apparatus additionally includes an optical means operative to measure at least one optical parameter. Where optical means is present, the apparatus includes at least one optical beam source and at least one optical beam detector.

Further, in accordance with another embodiment of the apparatus of the present invention, the cylindrical standing wave resonator is a cylinder acoustically coupled to the at least one acoustic standing wave generating source. The at least one acoustic standing wave generating source comprises at least one pair of piezoelectric transducer elements, each transducer element shaped as a segment of a cylinder.

In yet another embodiment of the apparatus, the at least one acoustic standing wave generating source is two generating sources, each disposed at 90° from the other, each source comprised of at least one piezoelectric transducer element.

In another embodiment of the apparatus the electronic circuitry includes means to cycle through multiple frequencies with which to actuate the at least one acoustic generating source and thereby producing multiple cylindrical standing waves for concentrating and aggregating the large particles at the central node of the waves.

These and other objects, features and advantages of the present invention will become apparent in light of the detailed description of the embodiments thereof, as illustrated in the accompanying drawings.

BRIEF DESCRIPTION OF THE DRAWINGS

The present invention will be understood and appreciated more fully from the following detailed description taken in conjunction with the drawings in which:

FIG. 4B1-4B3 shows three standing waves generated by the apparatus shown in FIG. 4A;

FIG. 4C1-4C3 shows the particle distribution at various stages of the separation/aggregation process produced by the apparatus of FIG. 4A;

Similar elements in the Figures are numbered with similar reference numerals.

DETAILED DESCRIPTION OF PREFERRED EMBODIMENTS

Figure 1A:
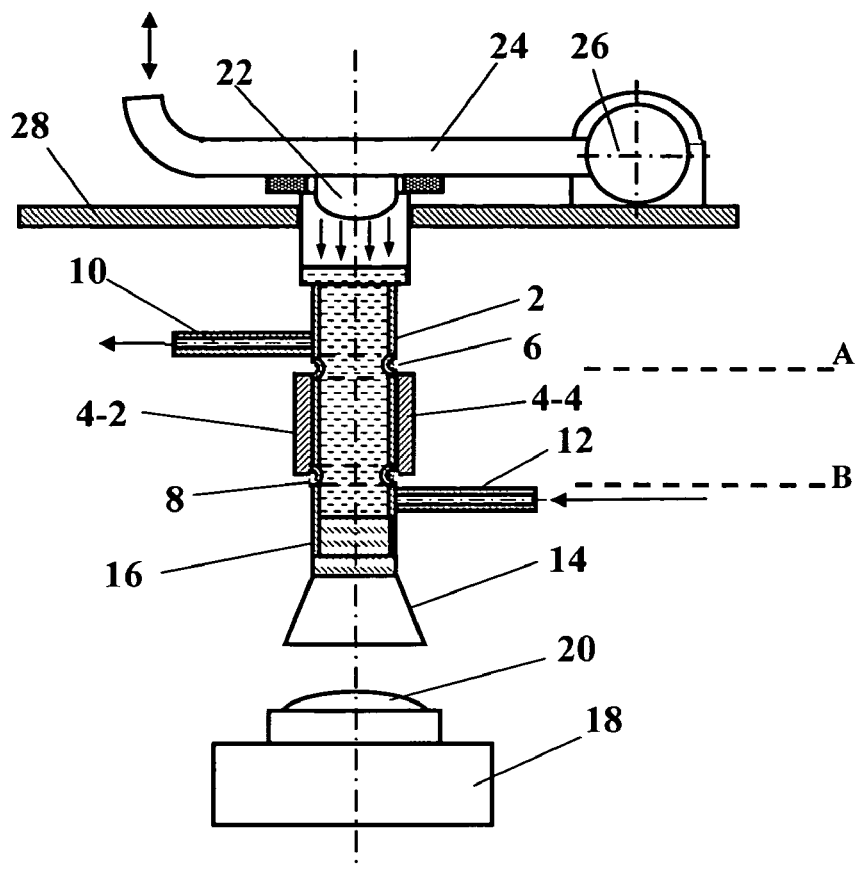
FIG. 1A is a side view of an apparatus constructed according to an embodiment of the present invention.

The present invention provides a method which employs standing acoustic waves to separate and concentrate large particles in a multi-component system before determining their concentration. The present invention also provides an apparatus which uses acoustic standing waves to separate the large particles whose concentration is to be determined. Concentration and aggregation typically occurs at the nodes of the standing wave. Specificity and sensitivity of the concentration determination is increased because of the at least hundred-fold increase in concentration of the large particles whose concentration is to be determined resulting from the step of separating/concentrating/aggregating.

The apparatus includes an acoustic standing wave manipulating device (ASWMD) which is comprised of a hollow acoustic standing wave resonator, typically a cylindrical resonator, and an acoustic wave generating source. The apparatus is operated without the need for a reference standing wave resonator and without the need for very exact temperature control as in U.S. Pat. No. 6,920,399. Temperature control may be at least a factor of ten less exacting than in prior art methods and apparatuses because both the sample and reference measurements are made essentially concurrently in the same resonator cavity.

The above mentioned patent is incorporated herein by reference in its entirety. Such incorporation is not to be construed as an admission of its being prior art vis-a-vis the present invention.

In what is described herein, the large particles whose concentrations are to be measured generally fall into the 50 nm to 500 micron size range, preferably in the range of about 500 nm to about 50 microns. The multi-component system will typically be a suspension or emulsion which may include biological or biochemical systems. However, the present invention is not intended to be limited to such systems and the invention may be used with other types of multi-component systems such as foodstuffs, wastewater, fuels, lubricants and biological fluids.

When the term "acoustic waves" is used herein above and below it typically, but without being limiting, refers to "ultrasonic waves".

In what is discussed herein above and below, the terms "separating", "concentrating" and "aggregating" and other such similar terms are being used interchangeably without any attempt at distinguishing between them except where explicitly noted or evident from the context of the discussion.

The hollow resonator of the apparatus of the present invention requires constrictions and/or bulges, typically integrally formed in the resonator walls. These constrictions and/or bulges around the cylinder's walls will herein be referred to as non-interference bands. These bands are positioned at the ends of the resonator region to which the acoustic wave generating source(s) is (are) attached and acoustically coupled. These constrictions and/or bulges prevent interference between acoustic waves traveling within the resonator walls and the standing waves generated within the resonator cavity. They therefore allow for relatively sharp large particle separation and aggregation within the resonator cavity.

More specifically, the invention provides for cycling the acoustic standing wave resonator, typically an ultrasonic standing wave resonator, between at least two operational ultrasonic acoustic frequencies and/or intensities. These frequencies and/or intensities also sometimes may be referred to herein as operational modes. One of the at least two operational modes acts to concentrate and/or aggregate a component of interest in the central region of the resonator cavity while creating a particle free reference region near that central region. Alternatively, large particle concentration and/or aggregation may be effected along the nodes of a standing wave in one direction, such as along the x-axis, while there is reduction or depletion of the large particles in another direction, such as along the y-axis. In both of these particle distributions, a second of the at least two operational modes measures one or more acoustical parameters of the sample containing the aggregated species.

Measurement of the concentration is affected by a means for measurement which can be an ultrasonic measurement system but may often also include an optical measurement system. It should be readily apparent to one skilled in the art that optical methods are to be considered non-limiting and other measuring methods are also possible. These alternative measurement methods include, but are not limited to, electrical conductivity, thermal conductivity, and calorimetry.

The method of the present invention comprises the following steps: separating and concentrating and/or aggregating the particles by size across the cavity of an acoustic standing wave resonator using at least one frequency generated by an acoustic wave generating source; measuring parameters, typically, but without being limiting, acoustic parameters and often also optical parameters, of the aggregated large particle sample and reference regions in the cavity of the acoustic standing wave resonator; and determining particle concentration from the data obtained from the parameter measurements in the step of measuring. The method contemplates separating particles by size using a flow-through system, but measurement on a static system is also possible. When optical parameters are measured the anisotropy of these parameters may be measured as well.

Before explaining at least one embodiment of the invention in detail, it is to be understood that the invention is not limited in its application to the details of construction and the arrangement of the components set forth in the following description, or illustrated in the accompanying drawings. The invention is capable of other embodiments, or of being practiced or carried out in various ways. Also, it is to be understood that the phraseology and terminology employed herein is for the purpose of description and should not be regarded as limiting.

FIG. 1A, to which reference is now made, shows a schematic side view of an apparatus constructed according to an embodiment of the present invention. The apparatus includes an ASWMD which is comprised of a hollow acoustic standing wave resonator 2, typically having a cylindrical shape, surrounded by, and acoustically coupled to, one or more acoustic wave generating sources, typically as shown here segmented tubular (cylindrical) piezoelectric elements 4. Resonator 2 includes non-interference bands formed of constrictions 6 and 8 for isolating the area of the standing wave oscillations. This area is determined by the size of piezoelectric elements 4. The constrictions substantially isolate the standing waves inside the cavity of resonator 2 generated by elements 4 from acoustical waves traveling within the walls of resonator 2 in the direction of the long axis of the cylinder.

Connecting sleeves 10 and 12 serve as outlets and inlets, respectively for sample liquid flow. The lower end face of resonator 2 is plugged by stopper 14 and includes an optically transparent window 16. Stopper 14 can be removed when mechanically cleaning acoustic standing wave resonator 2 is necessary.

Connecting sleeves 10, 12 serve as outlets and inlets for sample liquid flow. In other embodiments, the sleeves may have means to stop flow and measurements may be made on static non-flowing samples.

A digital camera 18 with an optical lens 20 provides optical monitoring of the properties of the particles whose concentration is to be determined. The source of light 22 is fixed on joint hinge holder 24 which with joint hinge 26 is mounted on stand 28. When opening joint hinge holder 24, acoustic resonator 2 may be rinsed and cleaned when required.

A typical, but non-limiting, diameter of cylindrical acoustic standing wave resonator 2 is about 0.5 to about 50 mm and a typical, but non-limiting, acoustical frequency of the resonance oscillation is about 0.2 to 50 MHz.

Not shown in FIG. 1A is the electronic circuitry required to generate the standing waves that separate the large particles whose concentration is to be determined. Typically, separation is effected in anisotropic fashion. Suitable electronic circuitry will be discussed with reference to subsequent Figures.

Additionally, not shown in FIG. 1A are the usually required temperature control elements such as one or more Peletier elements, a thermostat, and other temperature regulating components. Their disposition may be as shown and described in U.S. Pat. No. 6,920,399. However, because of the method used for measurement in the present invention, temperature control can be at least ten times less exacting than that required in Patent '399. Temperature control can be maintained to within a degree Centigrade without unduly influencing the acoustical parameters to be measured.

Resonator 2, typically made of a metal, such as stainless steel, titanium, nickel, aluminum, and copper alloys, is acoustically coupled to a generating source of acoustic waves. The resonator discussed in the examples described herein are coupled to tubular (i.e. cylindrical) segments of piezoelectric material such as lead zirconate titanate. It is readily understood by one skilled in the art that other piezoelectric materials may also be used. In addition to metals, resonator 2 may also be fabricated from glass, ceramics, or polymers.

It is to be understood that the faces of the piezoelectric segments must be coated with a conducting material such as silver so that they may be electrically connected to elements in the electronic circuits shown in the Figures to be discussed below.

In another embodiment, the resonator may be a radially polarized cylindrical piezoelectric tube. Such piezoelectric tubes, as well as piezoelectric transducers of other shapes, can be obtained commercially from PI Ceramics (Karlsruhe, Germany) and Piezopribor (Rostov-on-Don, Russia).

FIG. 1A shows non-interference bands formed by constrictions 6 and 8 at the ends of the resonator. As noted above, the constrictions reduce the interference of generated acoustical waves traveling in the walls of the resonator in the direction of the resonator's long axis. Without such a constriction, waves traveling along the long axis would interfere with the standing waves within the resonator cavity and interfere with the clean separation of the desired particles in the multi-component system. It should be noted that instead of constrictions as shown in FIG. 1A, bulges at both ends of the resonator cavity could also be present. These also would serve to reduce interference between the acoustic waves traveling in the resonator walls and the standing waves formed in the cavity of resonator 2.

In some embodiments, both a bulge(s) and constriction(s) may be used. In yet other embodiments, more than two bulges and/or constrictions may be employed. This latter embodiment is often found when multiple pairs of transducers are positioned along, and adjacent to, the walls of the resonator, for example as shown in FIG. 6D to be discussed below.

In other embodiments, instead of a digital camera as an optical monitoring element, a visible spectrometer or other optical measuring device may be used. Included among the other optical monitoring instruments which may be used are near infrared, fluorescence and luminescence spectrometers. The source of optical irradiation may be an infrared radiation, a visible radiation, or an ultraviolet radiation source. The radiation to be used will often be dictated by the nature of the particles to be separated.

While FIG. 1A shows an optical device for measuring concentration, the present invention, as will be discussed below, also, and primarily, contemplates use of acoustic measurement means. This acoustic measurement means is based on piezoelectric transducers which can be used to measure changes in ultrasound velocity, ultrasound attenuation and acoustical impedance. Such acoustic means may be used alone or in conjunction with optical means to determine particle concentration. Therefore the optical elements in FIG. 1A are not essential for the present invention. In fact it is contemplated that other concentration determining means such as, but not limited to, electrical conductivity, thermal conductivity, and calorimetry may be used in place of the optical means, but in conjunction with acoustic measurement means.

Figure 1B:
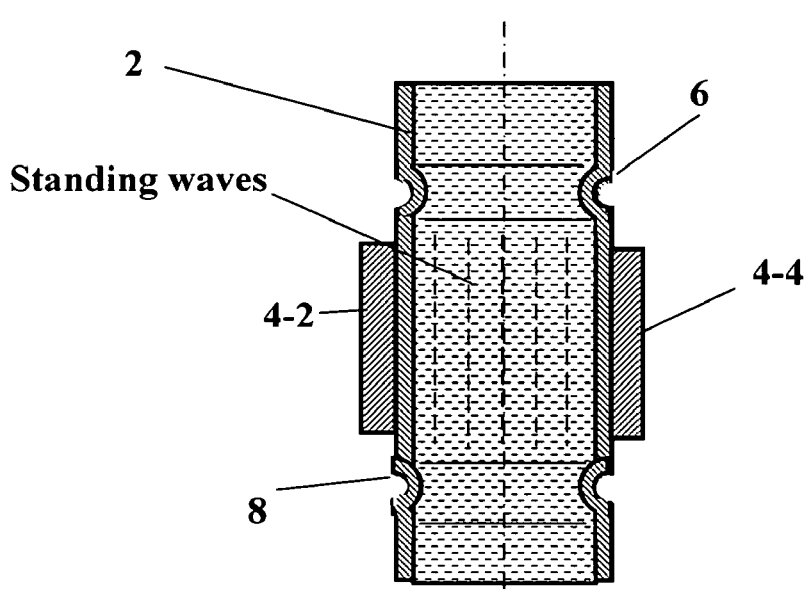
FIG. 1B is an enlarged view of the resonator and standing wave generating source in the apparatus of FIG. 1A.

FIG. 1B shows an enlarged view of resonator 2 presented in FIG. 1A. In particular the non-interference bands 6 and 8, here constricted areas, should be noted. The remaining corresponding elements in FIG. 1B are numbered as in FIG. 1A. Conducting sleeves 10 and 12 shown in FIG. 1A are not shown in FIG. 1B.

Figure 1C:
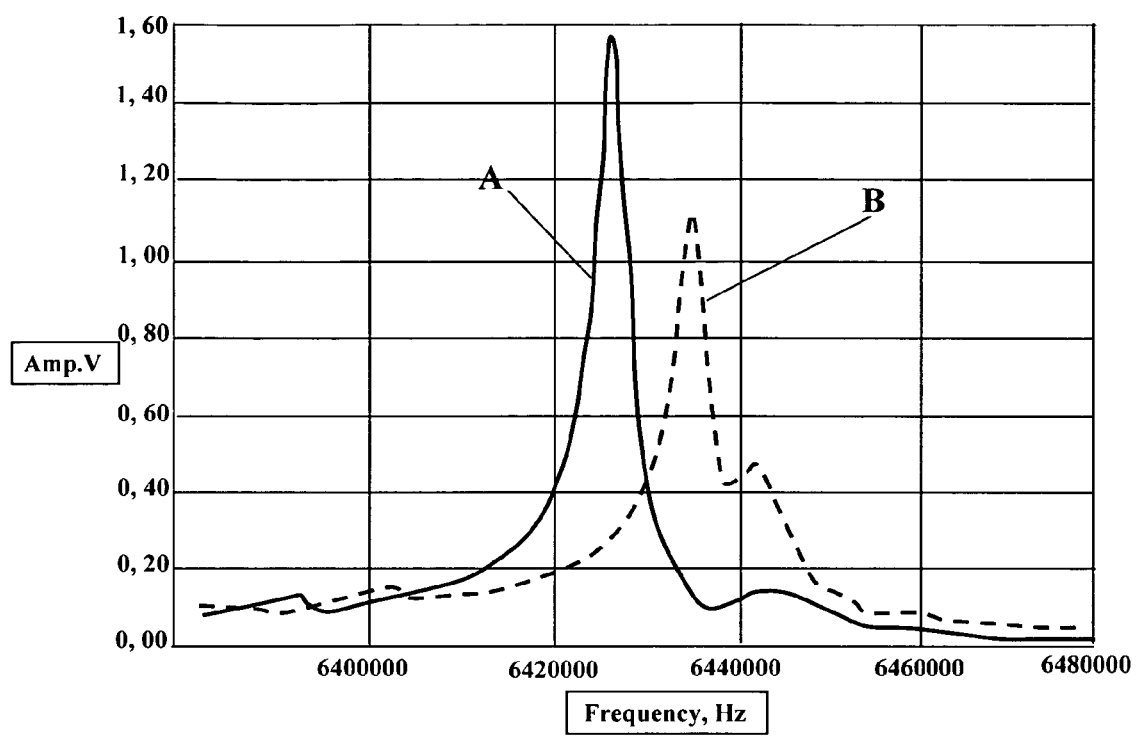
FIG. 1C is an amplitude versus frequency plot comparing the resonance peaks of the apparatus in FIG. 1A with the resonance peaks of a similar apparatus constructed according to prior art.

FIG. 1C shows an amplitude versus frequency plot for the resonator in FIGS. 1A and 1B. This type of plot relates to the Q-factor of a resonator, a figure of merit to be discussed further below. The resonator in FIGS. 1A and 1B includes non-interference bands which increase the symmetry of the resonator's resonance frequency peak as well as increase the amplitude of the resonance peak, as shown by the plot designated by A. A resonator without non-interference bands produces an asymmetric plot denoted as B in FIG. 1C with an amplitude only about two-thirds of that produced by the resonator in FIGS. 1A and 1B.

Figure 2A:
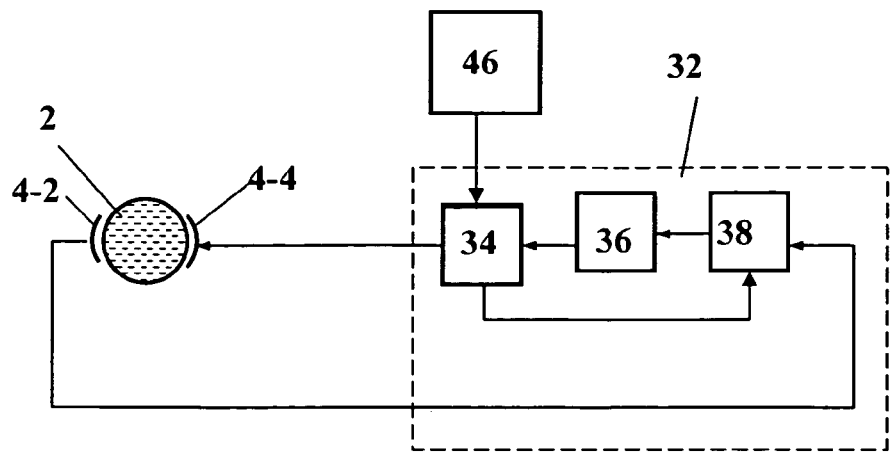
FIG. 2A schematically shows an apparatus constructed according to another embodiment of the present invention.

Reference is now made to FIG. 2A which shows electronic circuitry for use with a cylindrical acoustic standing wave resonator 2 and a single pair of piezoelectric transducer elements 4-2 and 4-4 constructed according to an embodiment of the present invention.

In the embodiment shown in FIG. 2A, only one transmitting piezoelectric element 4-2 and one receiving piezoelectric element 4-4 are present. These partially envelope acoustic standing wave resonator 2. Electronic circuit 32 assists in generating acoustical standing wave oscillations, typically ultrasonic oscillations. Circuit 32 includes a voltage controlled oscillator (VCO) 34, an electronic filter 36, and a phase detector 38. Phase detector 38 receives inputs from receiving piezoelectric element 4-2 and VCO 34. VCO 34 is in communication with and controlled by processor 46. Processor 46 may be for example a CPU or PC. Among its many functions, processor 46 tracks frequency changes in the resonator cavity arising from the sample as a relative change in the initial frequency.

VCO 34 is also in communication with and inputs a processor-determined frequency to transmitting piezoelectric element 4-4. Filter 36 receives signals from phase detector 38 and forwards the filtered signal on to VCO 34. The CPU or PC controls the frequency of the wave being generated and transmitted to resonator 2 via transmitting piezoelectric element 4-2. An optional amplifier may be placed between resonator 2 and voltage controlled oscillator (VCO) 34. Using the embodiment of FIG. 2A, the cylindrical acoustic standing wave field aligns and concentrates a significant portion of the desired particles of the sample along the x-axis of resonator 2 in the form of aggregates 30 (FIG. 2C).

Figure 2B:
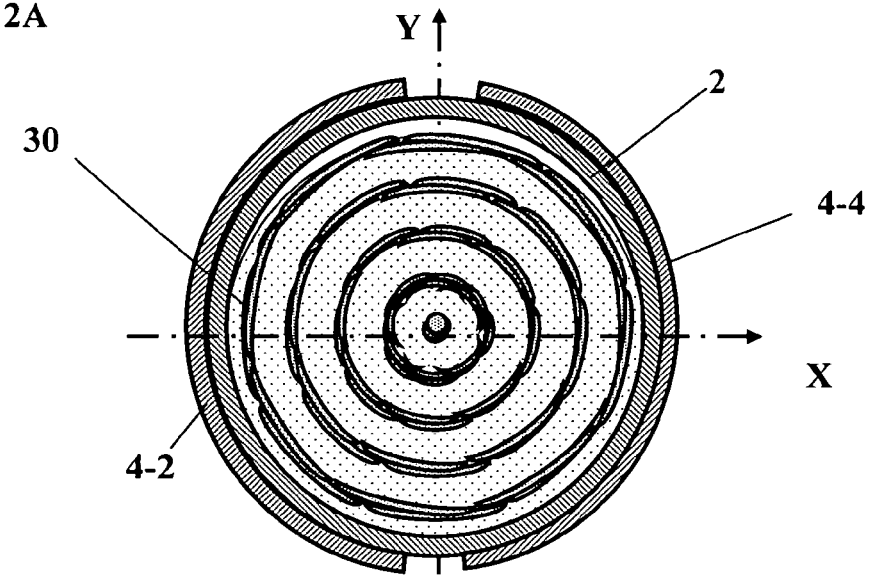
FIG. 2B shows the particle distribution generated by the apparatus of FIG. 2A.

Reference is also made to FIG. 2B which presents a view of the distribution of the separated large particles using cylindrical resonator 2 with a single pair of piezoelectric transducer elements 4-2 and 4-4 constructed according to the embodiment of FIG. 2A. The pair of transducers in FIG. 2B almost entirely encompass resonator 2. Because of this condition, the distribution of the large particles is substantially isotropic and consists of concentric ring structures when transducers 4-2, 4-4 generate high intensity acoustic waves. Each ring consists of a series of large particle aggregates 30 positioned at the nodes of the standing waves. Even though what is discussed herein is discussed in terms of aggregation at the nodes of the standing waves, in other instances aggregation may occur at the antinodes of the waves. This is typically a function of the density and/or compressibility of the large particles as will be further discussed below in conjunction with FIG. 3.

Figure 2C:
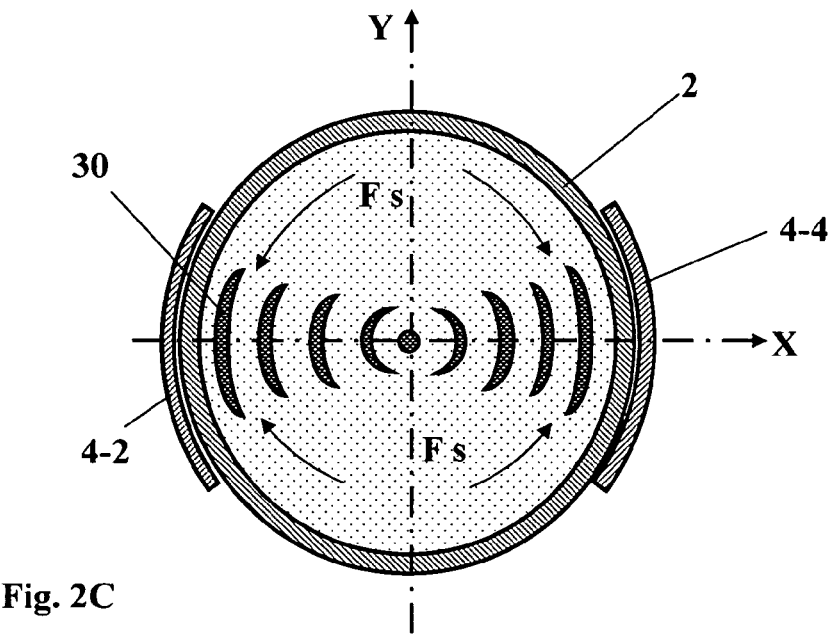
FIG. 2C shows the particle distribution generated by the apparatus of FIG. 2A wherein the transducer elements are smaller than those in the apparatus of FIG. 2B.

FIG. 2C, to which reference is now made, shows that the large particle aggregates are distributed as concentric rings 30 when viewed from the end (top) of the cylinder along its long axis. Each set of adjacent rings is separated by half the acoustic wavelength used. These rings represent the location of the separated and aggregated large particles for which a concentration measurement is desired. These rings appear at the nodes of the standing wave generated by piezoelectric elements 4-2 and 4-4 in the cavity of resonator 2. Transducer elements 4-2 and 44 in FIG. 2C are smaller than those in FIG. 2B and encompass a smaller fraction of the cylinder's lateral surface.

Even with the smaller transducers of FIGS. 2A and 2C, at low acoustical intensities one obtains a large particle distribution as in FIG. 2B. When acoustical intensity is increased the distribution of FIG. 2C is obtained.

The distribution in FIG. 2C is a result of the interaction of several forces. The total force acting on the particle can be thought of as resulting from primary and secondary acoustic forces. The primary force is produced by the acoustic wave and acts in the direction of its propagation. However, when two particles are present in the acoustic field, the total incident field on one particle includes the primary field plus a secondary field resulting from scattering of the acoustic waves from the second particle. This secondary force is shown in FIG. 2C as Fs. This secondary force arising from the interaction between the two particles when acting on rigid particles drives the particles to the nodal regions where they form clusters as in FIG. 2C. These rigid particles are substantially depleted from the region along the y-axis.

Figure 2D:
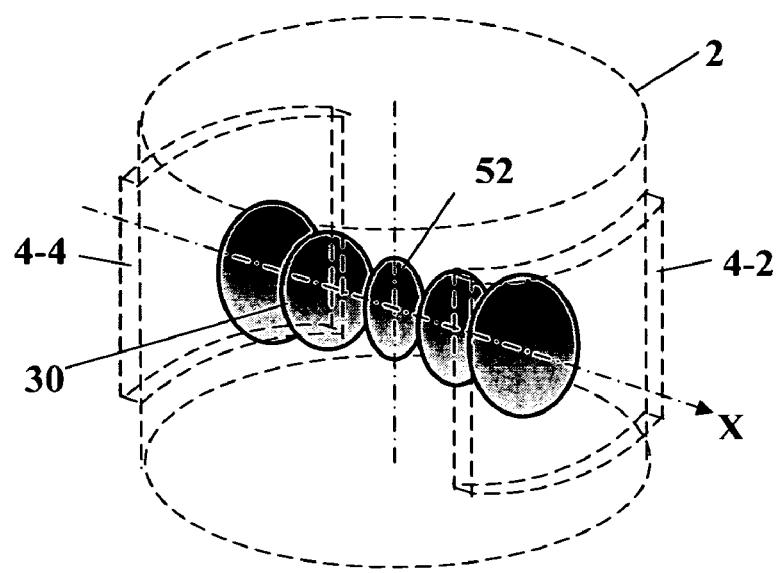
FIG. 2D shows a side view of the resonator of the apparatus constructed according to the embodiment of FIG. 2A with the large particle aggregates it generates shown at the nodes of the standing waves.

Reference is now made to FIG. 2D where a schematic side view of resonator 2 and transducers 4-2 and 4-4 are shown as well as the large particle aggregates 30 concentrated at the nodes of the standing wave generated in resonator 2. This Figure gives a better view of the aggregates 30 than FIG. 2C.

When using the system shown in FIG. 2A for organizing, i.e. concentrating and/or aggregating, the large particles, high intensity ultrasonic waves are required. These are generated by transducer element 4-2 and emitted through resonator 2. When making measurements of concentration based on acoustical parameters, waves of lower intensities are required and generated by transducer element 4-2. These lower intensity waves fail to organize, i.e. concentrate/aggregate, the large particles of the system at the nodes of the generated waves. The lower intensity reference measurement is also made along the x-axis in the embodiment of FIG. 2A (FIG. 2C).

While applying the apparatus in FIG. 2A to large particles, it should be understood that smaller particles, typically dissolved particles, are distributed substantially isotropically and their concentration can be determined using prior art methods, for example those found in U.S. Pat. No. 6,920,399.

Figure 3:
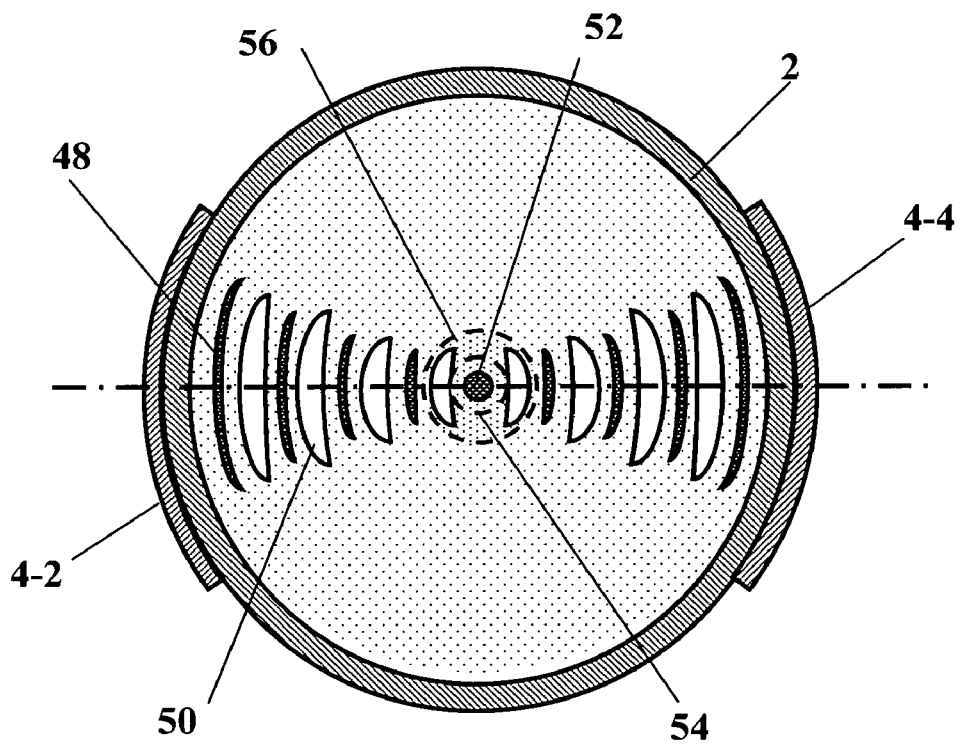
FIG. 3 shows the particle distributions of two types of large particles, each with a different density, separated by the apparatus of FIG. 2A.

FIG. 3, to which reference is now made, shows a view looking down the long axis of the resonator of FIG. 2A. FIG. 3 represents the separation of materials of different densities and compressibilities. The separation has been effected by a cylindrical resonator having a single pair of piezoelectric transducer elements constructed and operative according to the embodiment shown in FIG. 2A.

FIG. 3 shows that when separating particles of different densities and compressibilities in a multi-component system, high density rigid particles 48, having a density greater than that of water and a compressibility less than that of water, are concentrated in the areas of low amplitude, high acoustic pressure (nodes of the standing waves). Low density non-rigid material 50, having a density less than that of water and a compressibility more than that of water, are concentrated in the areas of high amplitude, low acoustic pressure oscillations (anti-nodes of the standing waves). As a result, aggregates of the particles form which enable their selective analysis. If optical analysis is used, one may limit the area of optical measurement to central node 52. The total number of particles is then proportional to the size of the aggregate at node 52.

Concentration measurements based on optical means, e.g. optical density measurements, may be made in the region of central node 52 and reference circle 54. The measurement near circle 54 serves as a reference measurement, while that made at node 52 serves as the sample measurement. However, when particle distributions similar to that in FIG. 2C are obtained and a single type of particle is aggregated, a digital camera can be used to measure concentrations over the entire resonance cavity.

The above optical measurements are used to measure the concentration of the material at central node 52. To measure the concentration of the material at the antinodes, that is the material at 50, i.e. the material less dense and more compressible than water, optical density measurements are made within the area of circle 56. A value for the less dense, more compressible material is obtained by subtracting the previous readings of the material within circle 54 and at central node 52 from the reading within circle 56.

Determination of the concentration of the particles in FIG. 3 above has been described as being effected by measurement of an optical parameter. It should readily be understood that measurement of one or more acoustical parameters may also be used to determine the concentrations of the two types of large particles shown in the Figure.

Acoustic measurements measuring changes in ultrasound velocity $\Delta v$ and ultrasound attenuation $\Delta \alpha$ of the sample and of the fraction enriched by high density (HD) and low density (LD) large particles may be made. Usually the sound velocity measurements are more sensitive for high density particles and sound attenuation is more sensitive for low density particles. The concentration of the high density and low density particles may be represented by % HD and % LD, respectively. These are related by two equations which include the two concentrations as the two unknowns.

$$\Delta v = D1(\% HD) + D2(\% LD)$$

$$\Delta\alpha = D3(\% HD) + (\% LD).$$

Since D1-D4 are constants obtained previously from analysis of samples having known compositions, % HD and % LD can be determined after measuring $\Delta v$ and $\Delta\alpha$.

Figure 4A:
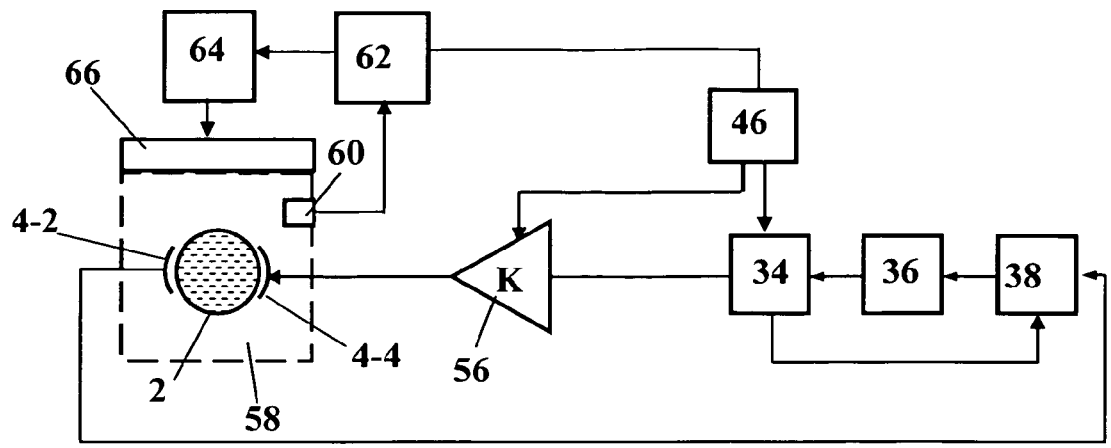
FIG. 4A schematically shows an apparatus constructed according to yet another embodiment of the present invention.

Reference is now made to FIG. 4A which shows an electronic circuit of another embodiment of the present invention. Acoustic standing wave resonator 2 is coupled to a single pair of piezoelectric transducer elements 4-2 and 4-4 as in FIG. 2A. Unlike FIG. 2A where only a single frequency is supplied, the electronic circuitry in FIG. 4A generates a multiplicity (two or more) of frequencies and intensities which in turn produce an anisotropic large particle distribution in the resonator cavity. These multiplicity of frequencies create Fourier series-like waveforms. There is continuous cycling between the frequencies. This cumulative waveform pushes substantially all of the large particles to be measured into the center of the cylindrical resonator. Other areas in the resonator are substantially devoid of the desired component and rings, as in FIG. 2C.

In FIG. 4A, phase detector 38, filter 36 and VCO 34 are in communication with each other and operate as in FIG. 2A. Therefore description of their operation will be omitted here. Processor 46, in addition to being in communication with VCO 34 as in FIG. 2A, is also in electronic communication with amplifier 56 through which transmission coefficients are varied and cycling of the emitted frequencies is effected.

Figure 4B:
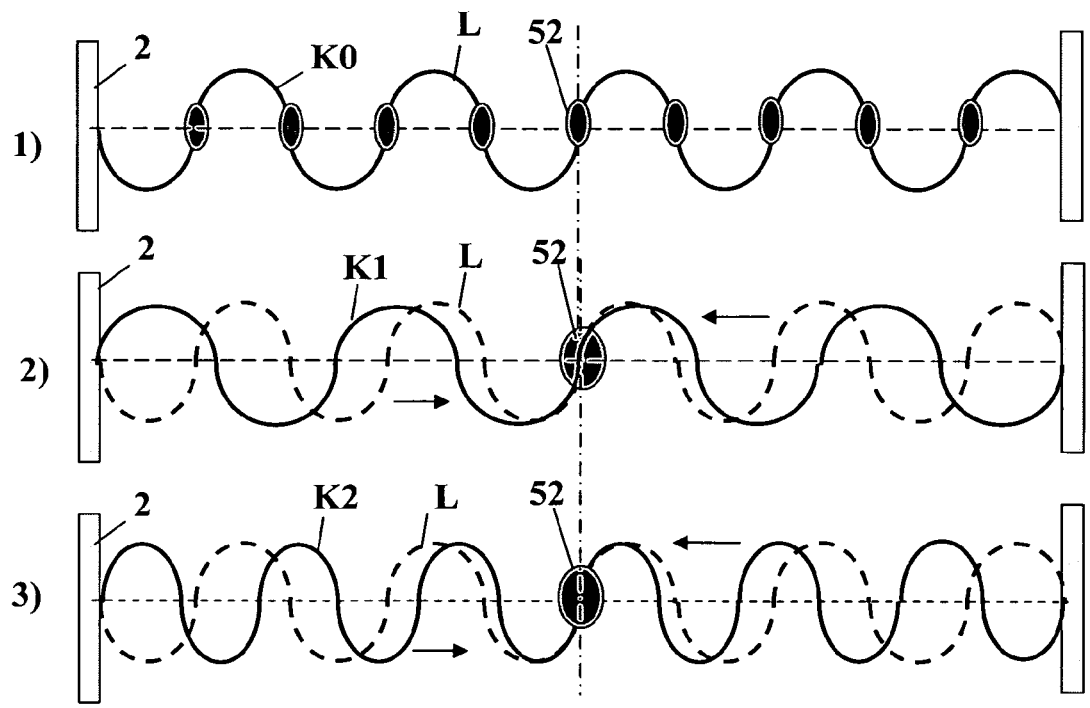

The multiplicity of frequencies are produced in amplifier 56 where transmission coefficient Kn is cyclically changed between K1, K2, K3, . . . In FIGS. 4B1-4B3, L represents the base wave. This multiplicity of frequencies generates a Fourier series-like waveform leading to anisotropy in the distribution of the large particles in the multi-component system. The smaller particles, typically dissolved particles, are distributed substantially isotropically and their concentration can be determined by prior art methods, for example those found in U.S. Pat. No. 6,920,399.

FIG. 4A shows a typical, but non-limiting, temperature control assembly. It includes a thermal jacket 58 in thermal communication with a Peltier element 66. Control is effected by processor 46 in electronic communication with temperature controller 62, the latter further in electronic communication with amplifier 64. Amplifier 64 controls Peltier element 66 based on feedback from thermal sensor 60 as to the temperature within thermal jacket 58.

A temperature control assembly such as that shown in FIG. 4A may be used with the systems in FIGS. 1A, 2A and 5A, the latter to be discussed below, although not shown there. Such assemblies are used to control temperature even though temperature control need not be as exacting as with prior art methods. It should be noted that in some embodiments the temperature control assembly may be dispensed with entirely. Since both sample and reference measurements are measured within the same apparatus essentially concurrently, temperature stability requirements need not be as exacting as in prior art. As noted above, when ultrasonic measurements are made on the reference, they are made by cycling between reference and sample measurements in 0.1 sec. Prior reference measurements often take several minutes to perform and are usually performed on different sample volumes than the actual sample measurement.

Referring to FIGS. 4B1-4B3, several standing waves are presented each derived using a different transmission coefficient, Kn. FIG. 4B1 shows the base standing wave with coefficient K0. FIGS. 4B2 and 4B3 show additional standing waves based on transmission coefficients K1 and K2, each being out of phase with each other and out of phase with the base wave shown in FIG. 4B1. All the waves, however, have the same central node 52 and have an even number of half wavelengths along the diameter of the cylindrical resonator. The large particles whose concentration is to be determined will concentrate and/or aggregate at central node 52, while at other points in the sample the large particles will be distributed isotropically due to interference between the various waves. It should readily be understood that the number of acoustic waves that can be used with the apparatus of FIG. 4A may exceed three.

In FIGS. 4C1-4C3, we see the effect of this multiplicity of generated standing waves on the distribution of the large particles. FIGS. 4C1 and 4C2 are identical to FIGS. 2B and 2C described above where only a single separating acoustic wave is used. They represent the initial phases of the separation, i.e. concentration and/or aggregation, process and the effects of the primary and secondary acoustic forces as discussed above in conjunction with FIG. 2C. FIG. 4C3 shows the effect of a plurality of separating acoustic standing waves with a common central node. Concentration and/or aggregation of the large particles occurs at that node with the interference patterns of the multiplicity of waves leaving a very much more isotropic distribution elsewhere in the sampling chamber. In sum, a multiplicity of waves each with different frequencies allows for greater concentration and/or aggregation of the large particles being measured.

Figure 5A:
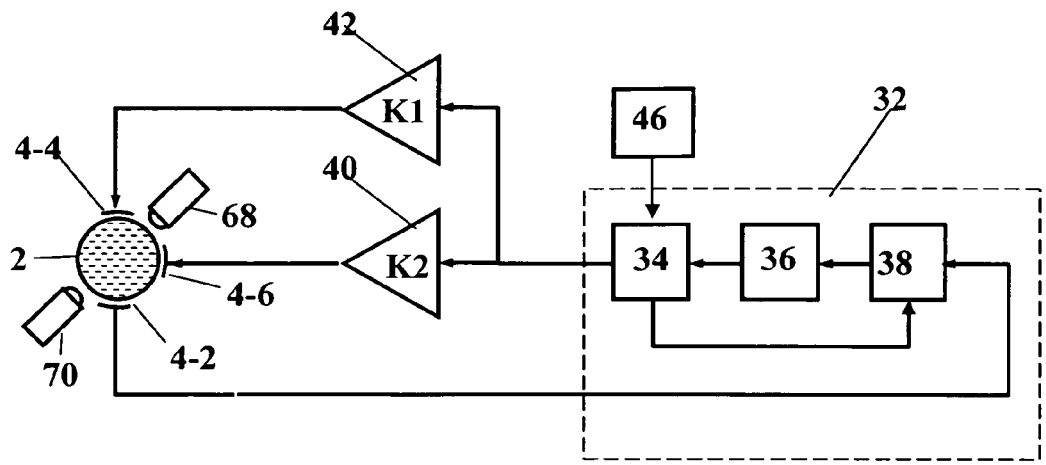
FIG. 5A schematically shows an apparatus constructed according to yet another embodiment of the present invention.
Figure 5B:
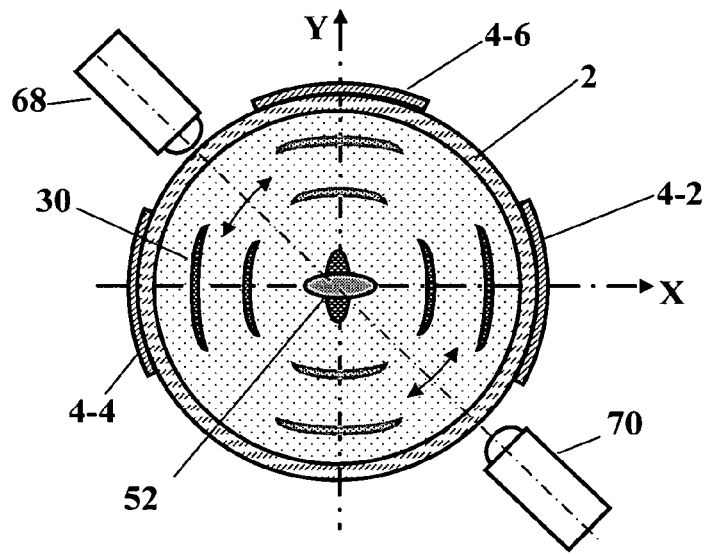
FIG. 5B shows the particle distribution generated by the apparatus of FIG. 5A.

FIG. 5A, to which reference is now made, shows the electronic circuitry used with a cylindrical resonator employing three piezoelectric transducer elements 4-2, 4-4 and 4-6 constructed according to a third embodiment of the present invention. FIG. 5B presents a view of the distribution of the separated large particles using a cylindrical resonator with three piezoelectric transducer elements constructed according to the embodiment shown in FIG. 5A.

The circuit shown in FIG. 5A is similar to the circuit in FIG. 2A and identical elements have been given the same numbers. Since these identical elements are operative in a manner identical to those in FIG. 2A, their further description will be omitted here.

In addition to the elements present in FIG. 2A, FIG. 5A includes a third piezoelectric transducer element, transmitting transducer 4-6 and buffer amplifiers 40 and 42. Additionally, there is an optical beam source 68 and an optical beam detector 70 positioned as shown in the Figure.

Amplifiers 40 and 42 have transmission coefficients K2 and K1 respectively, where typically, but not necessarily, K1≠K2. The different frequencies and/or intensities inputted from amplifiers 42 and 40 to transducer transmitters 4-4 and 4-6 respectively lead to an anisotropic distribution of the large particles whose concentration is to be measured.

Amplifiers 42 and 40 are operated cyclically at the control and command of processor 46 via VCO 34. These amplifiers cyclically activate transducers 4-4 and 4-6. Aggregates 30 align along the x-axis when transducer 4-4 is activated and along the y-axis when transducer 4-6 is activated (see FIG. 5B). Because of this continuous cycling, the length of each cycle typically being 0.1 second, the aggregates 30 move between the axes as indicated by the arrows in FIG. 5B. As the particles cycle between the axes they do not become disaggregated requiring subsequent re-aggregation.

As aggregates 30 move between the axes they move through the beam of optical beam source 68 and concentration measurements can be made. Additionally, acoustical parameter measurements are made with transducers 4-4 and 4-2 at lower acoustical intensities than the intensities used for particle separation and concentration. The measurements are similar to the acoustical measurements made with the apparatus of FIG. 2A.

Separation of the large particles into aggregates 30 is effected by transmitting transducer elements 4-4 and 4-6 in FIG. 5A operating at high acoustic intensities. Separation is effected by aligning the particles primarily in the direction between the piezoelectric transducer element having the higher voltage, which generates a higher acoustic intensity. The frequency of the acoustic standing wave in resonator 2 which is used to separate and to concentrate/aggregate the large particles is typically about 0.2 to about 50 MHz. Generally, a decrease in size of the rigid particles to be separated requires a higher frequency acoustic standing wave.

Processor 46 operates both transmitting transducer elements 4-4 and 4-6 in the separation and measurement steps. Processor 46 via VCO 34 through amplifiers 40 and 42 cyclically switches between piezoelectric transducer elements 4-4 and 4-6 and forwards signals received at these elements to phase detector 38 via receiving transducer 4-2. Cycling between the low and high frequencies, or equivalently between low and high acoustical intensities, typically occurs over a time duration of 0.1 sec.

In FIG. 5A, transmitting transducers 4-4 and 4-6 are used to separate, i.e. concentrate and aggregate, the large particles at high acoustic intensity, typically at about 1 to about 30 $W/cm^2$, preferably about 10 $W/cm^2$. For the acoustic parameter measurements, both transducers 4-4 and 4-6 use one or more lower acoustic intensities, typically about 0.01 to about 1 $W/cm^2$, preferably about 0.1 $W/cm^2$.

FIG. 5B shows the distribution of the large particles to be measured after application of the concentrating/aggregating standing waves generated using the embodiment shown in FIG. 5A. Referring to the axes shown in FIG. 5B, sample concentration measurements are made along the x-axis when aggregates 30 are aligned along the x-axis. Reference measurements are made along the x-axis when aggregates 30 are aligned along the y- axis, that is when transducer 4-6 is activated.

The optical measurements noted above are made along the line between optical beam source 68 and optical beam detector 70. The measurement in effect represents the time averaged concentration of the particles being measured along that line. The results of these measurements are compared to similar optical measurements of samples with known concentrations.

The apparatus in FIG. 5A is used to determine the concentration of the large particles. It should be understood that smaller particles, typically dissolved particles, are distributed substantially isotropically and their concentration can be determined using prior art methods, for example those found in U.S. Pat. No. 6,920,399.

Figure 5C:
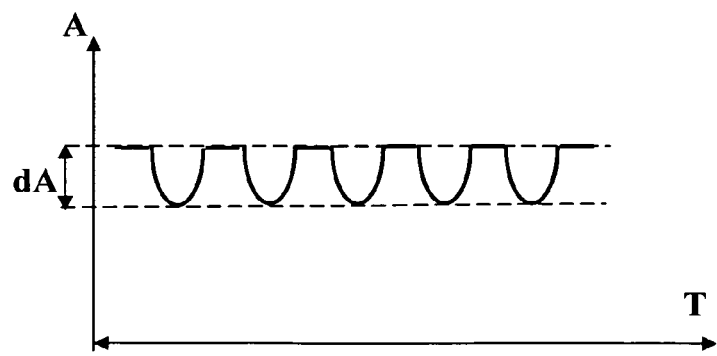
FIG. 5C shows the time dependency of a parameter measured with the apparatus of FIGS. 5A and 5B.

FIG. 5C shows the time dependency of the parameter being measured with the system constructed and described in conjunction with FIGS. 5A and 5B. As noted above, the parameter may be either an optical or acoustical parameter; in either case, the value of the measured parameter varies with time as the concentrating/aggregating process is effected by cycling the separating/concentrating operational mode between transducers 4-4 and 4-6.

Figure 6A:
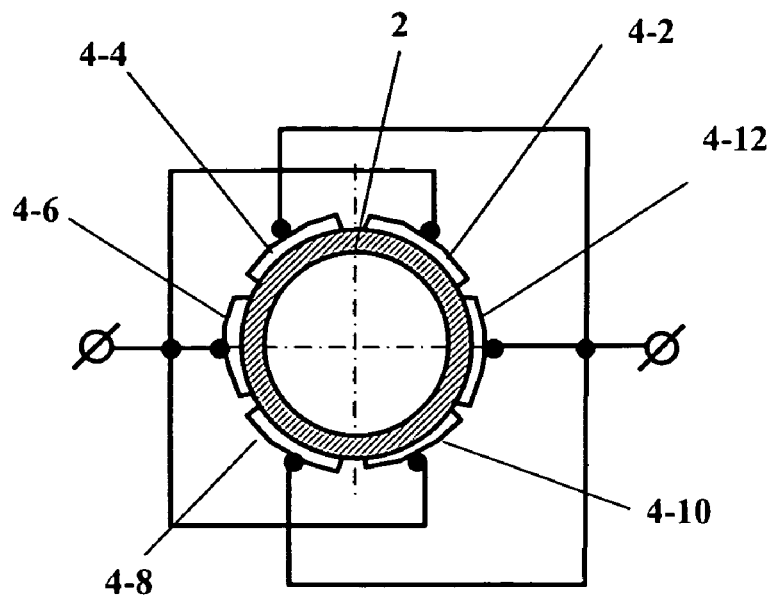
FIG. 6A shows a cylindrical resonator with three pairs of piezoelectric transducer elements.
Figure 6C:
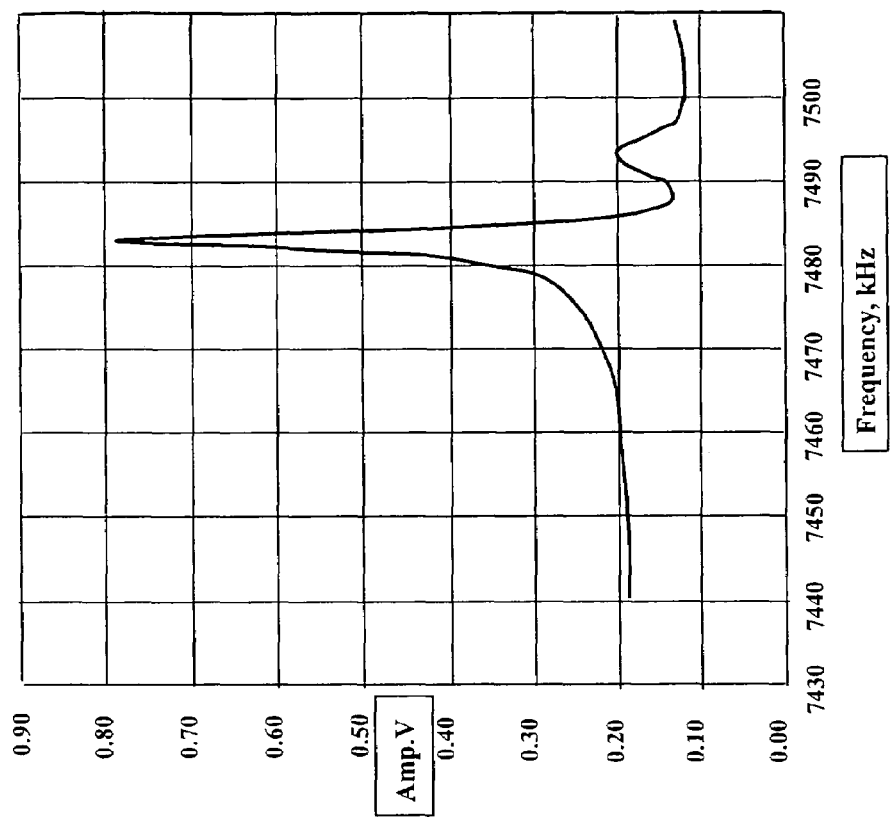
FIGS. 6B and 6C show amplitude versus frequency plots, respectively, for a cylindrical resonator with a single pair of piezoelectric transducer elements constructed according to the embodiment of the present invention shown in FIG. 2A and for a cylindrical resonator with three pairs of piezoelectric transducer elements constructed as in FIG. 6A.
Figure 6B:
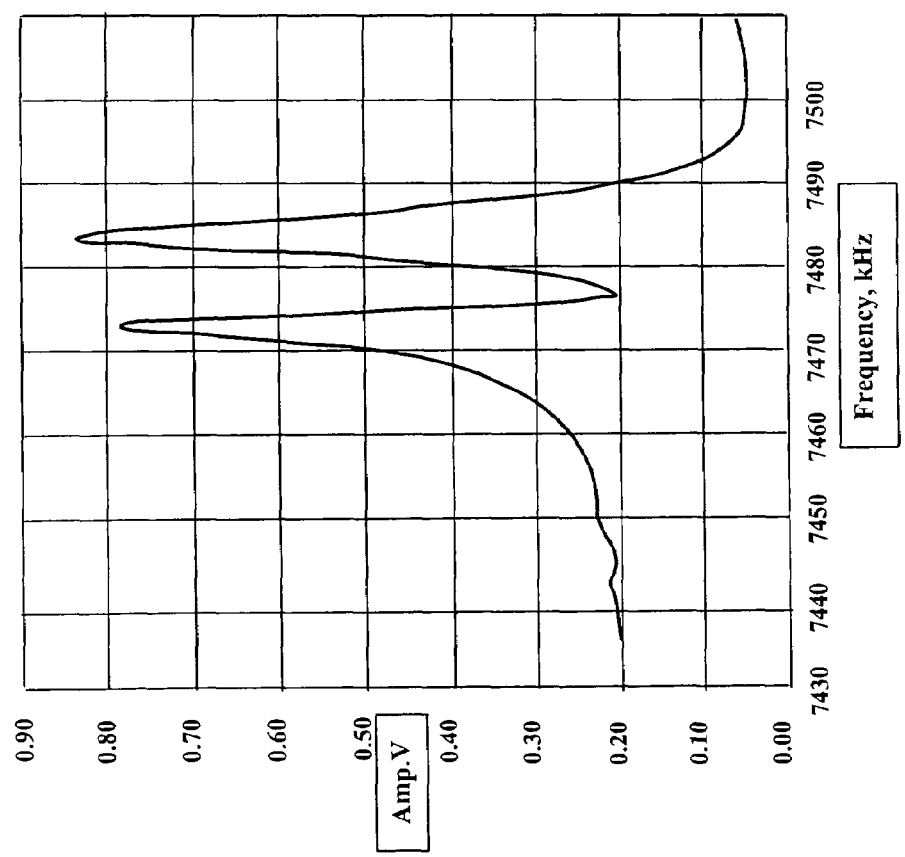
Figure 6D:
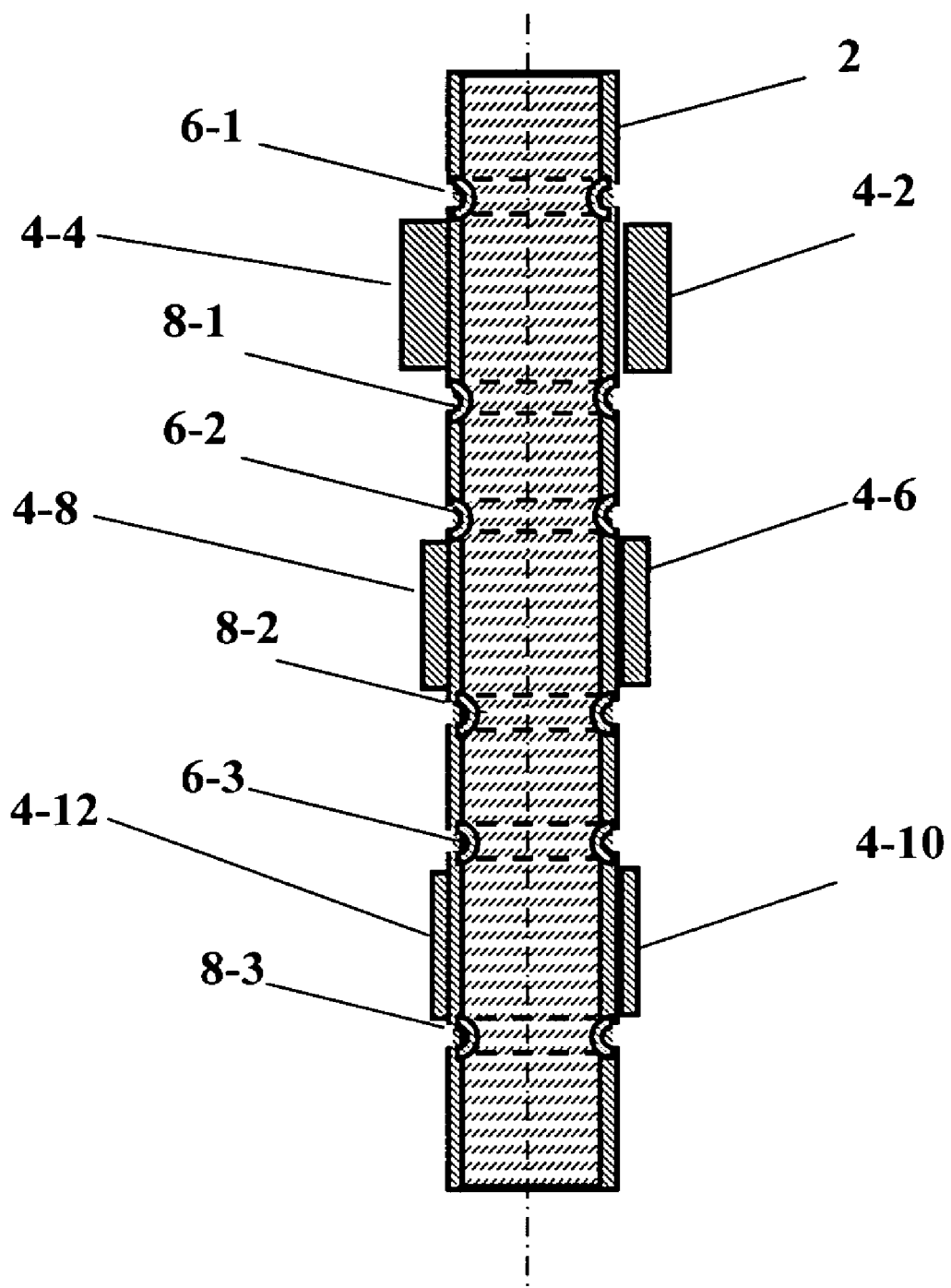
FIG. 6D shows a resonator with multiple pairs of transducer elements, the resonator useful for separating several components of a multi-component system.

Reference is now made to FIGS. 6A-6C. FIG. 6A shows a resonator system having three pairs of piezoelectric transducer elements, 4-2 through 4-12, around a cylindrical acoustic standing wave resonator 2 similar to those shown in FIGS. 1A, 2A and 4A. The increased number of transducer pairs vis-à-vis the systems in FIGS. 1A, 2A and 4A improves the quality of the resonance characteristics of the resonator. This is evident when comparing the resonator's Q-factor which increases with an increased number of transducers.

The Q-factor of a resonator is equal to the resonance frequency divided by the frequency spread at half power (half-amplitude). Q is inversely proportional to the total energy loss in the resonator system, which results inter alia from attenuation due to the liquid in the resonator cavity, scattering, friction, imperfect reflection, and improper transducer mounting and coupling. High Q-factors are reflected in the symmetry and smoothness of the resonance peaks and well-defined separation of resonance peaks in amplitude versus frequency plots.

FIG. 6B shows an amplitude versus frequency plot when a single pair of transducers is used while FIG. 6C shows the sharper peak (alignment of the amplitude frequency response) when three pairs of transducers are used, as in the resonator system of FIG. 6A. Additionally, the amplitude of the resonance peak of the resonator with a multiplicity of pairs of transducers (FIG. 6A) is about a third larger than a resonator with a single pair of transducers (e.g., FIG. 2A). Additionally, when an increased number of transducers is used, the amplitude-frequency response is less influenced by any elliptical deviations in the cross section of a cylindrical resonator. Therefore, lower mechanical precision is required in the resonator's construction. The higher Q value also allows for a more efficient particle separation and concentration at the nodes of the standing waves. This concentrating effect can produce a concentration increase exceeding 100 times the original isotropic pre-aggregation concentration with a concomitant increase in the specificity and sensitivity of the analysis.

Reference is now made to FIG. 6D which shows a resonator for separating several large particle components of a multi-component system and measuring their concentrations. The resonator shown in the Figure may also be a side view of the resonator shown as a top view in FIG. 6A.

Resonator 2 of FIG. 6D has three distinct measuring chambers each intended to separate and measure a different size component of the system. Resonator 2 has three pairs of transducer elements 4-2, 4-4; 4-6, 4-8; and 4-10, 4-12 disposed along the resonator 2 in the direction of its long axis. At each of the ends of the transducer elements, and separating each pair of elements from its nearest neighbor(s), are three pairs of non-interference bands, 6-1, 8-1; 6-2, 8-2; and 6-3, 8-3, here shown as constrictions. Each of the three pairs of transducer elements 4-2, 44; 4-6, 4-8; and 4-10, 4-12 is in electrical communication with an electronic circuit. In another embodiment, each pair of transducers may be in electronic communication with a different circuit. Each circuit allows the transducer pair to which it is connected to generate a standing wave of a different frequency and/or intensity, thereby separating particles of different sizes.

As noted above, resonator 2 in FIG. 6D can be used to separate particles of different sizes. Transducer pair 4-2 and 4-4 may be used to concentrate/aggregate and measure the concentration of the largest particles. Transducer element pair 4-6 and 4-8 may be used to concentrate aggregate particles of smaller, but still large size. The third pair of piezo-transducer elements 4-10 and 4-12 may be used to measure the solvent containing isotropically dispersed small dissolved particles.

When each pair of transducers is in electronic communication with a different circuit, each circuit is operated at a different frequency and/or intensity. When high intensity waves are used for segregating and aggregating the particles, the frequency generated by transducer pair 4-2, 4-4 will be lowest as the resonator section between these transducers is intended to separate the largest particles. When low intensity waves are being produced for acoustical parameter measurements, the frequency generated by transducer pair 4-10, 4-12 will be highest as the resonator section between them is intended to effect a reference measurement of the solvent containing small isotropically dispersed or dissolved particles. When a single electronic circuit activates the three pairs of transducers, the frequency and/or intensity is cycled every 0.1 second or less and the three pairs of transducers are actuated cyclically each with its appropriate separating mode frequency and/or intensity.

Figure 7:
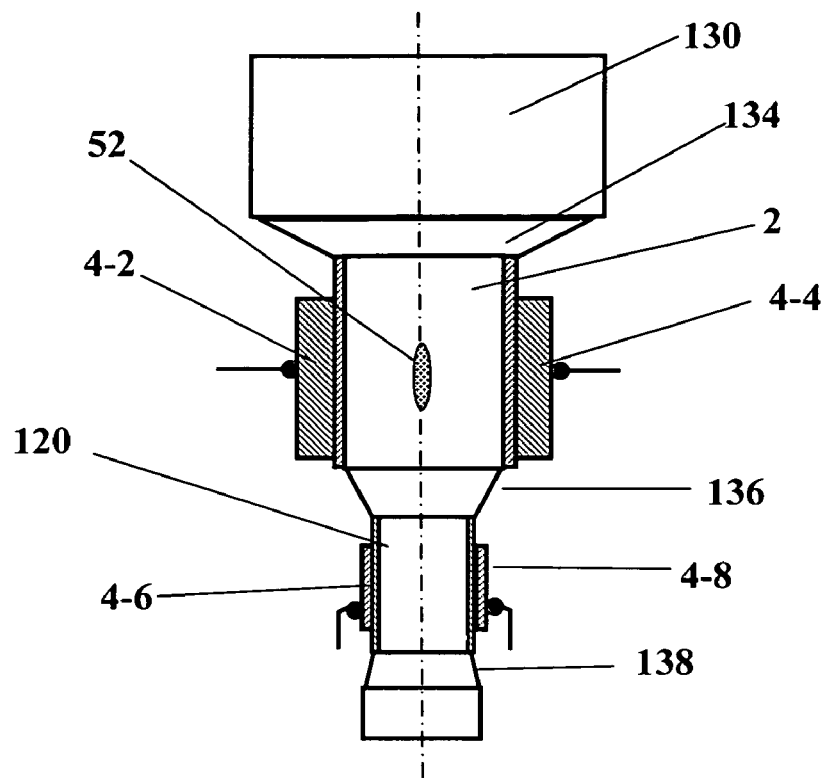
FIG. 7 shows an apparatus constructed according to the present invention according to yet another embodiment of the invention.

In FIG. 7, to which reference is now made, an apparatus constructed according to another embodiment of the present invention is shown. A pair of transducer elements 4-2 and 4-4 is disposed around a cylindrical acoustical resonator 2. The transducer elements are connected to an electronic circuit (not shown) similar to the one presented in FIG. 4A and discussed above. The circuit cycles through a plurality of frequencies and intensities causing the large particles within the cavity of resonator 2 to concentrate/aggregate at its center 52.

In FIG. 7, element 130 is a solution reservoir. Constriction-shaped elements, 134, 136 and 138 positioned above and below resonators 2 and 120 (the latter discussed below) serve as non-interference bands.

A pump (not shown) is operative to draw the concentrated particles from the cavity of resonator 2 into a smaller acoustic resonator 120. Transducer elements 4-6 and 4-8 are disposed around, and in acoustical communication with, resonator 120. Transducer elements 4-6 and 4-8 are in electronic communication with an electronic circuit (not shown) different from the one that activates transducers 4-2 and 4-4.

Particles concentrated by high intensity acoustical waves are pumped from the center 52 of resonator 2 and move into resonator 120. There they become even more concentrated under the influence of high intensity acoustical waves generated by transducers 4-6, 4-8 because of the smaller volume of resonator 120. Acoustical measurement of the sample is effected by low intensity acoustical waves in resonator 120 and the measurement is carried out at acoustical intensities lower than those used to separate/concentrate the particles.

After the sample has been pumped from resonator 2 and into resonator 120, measurement of the reference solution is effected in resonator 2 using waves of low acoustical intensity. These waves are generated by transducers 4-2, 4-4 coupled to resonator 2. At that point, just residual solvent and relatively small amounts of background large particles remain in resonator 2.

After a concentration is determined in resonator 120, it can be adjusted to its true value, i.e. its concentration in reservoir 130, since the volume of resonator 120 relative to the volume of resonator 2 is known.

After separation of the component of the multi-component system has been completed, measurement and determination of the concentration of the component may be carried out.

The determination of concentration for large particles, that is particles with sizes ranging from about 50 nm to about 500 microns, may be made by measuring acoustical parameters. An apparatus constructed according to FIGS. 1A, 2A, 4A, 5A, 6D or 7 and described above may be used to measure acoustical parameters and their frequency and intensity dependence. When using acoustical parameters to determine the concentration of the large particles, the entire resonator cavity is acoustically scanned with ultrasonic waves.

With the apparatus constructed according to FIGS. 1A, 2A, 4A, 5A, 6D or 7, the resonance frequency of the sample is measured. It is known that concentration is related to the change in ultrasonic wave velocity. This in turn is related to the change in the resonance frequency peak in an amplitude versus frequency plot (e.g., FIGS. 1C and 6C) between the sample (here shown with subscript 1) and a reference (here shown with subscript 2). This relationship is given by the formula:

$(v_1-v_2) \sim (f_1-f_2) = MC$, where C is concentration, M a constant, $v_1$ and $v_2$ the ultrasonic wave velocity in the sample and reference, respectively and $f_1$ and $f_2$ the resonance frequencies of the sample and reference, respectively. The constant M is determined separately by calibration with suspensions, emulsions, etc. of known particle concentrations.

The resonance frequencies may be determined by identifying output-voltage maxima such as in FIG. 1C or 6C discussed above or by determining the inflection points of a phase-frequency plot.

Similarly, acoustic attenuation is related to concentration of the component by changes in the width at half-power of the frequency peak in the amplitude versus frequency plot according to the following relationship:

$(\alpha_1-\alpha_2) \sim (\delta f_1 - \delta f_2) = NC$, where C is concentration, N is a constant, $\alpha_1$ and $\alpha_2$ represent the acoustic attenuation of the sample and reference, respectively and $\delta f_1$ and $\delta f_2$ the difference in frequency band width at half-power of the sample and reference, respectively. Measuring $\delta f$ for the sample is typically achieved by using the phase detector to measure f at a phase of ±45°. The constant N is determined separately by calibration with suspensions, emulsions, etc. of known particle concentrations.

It should be noted that often it is enough to measure one of the two ultrasonic parameters, velocity or attenuation. For processes accompanied by density and elasticity changes, ultrasonic sound velocity is the more sensitive parameter; for processes accompanied by viscosity and heat capacity changes, ultrasonic attenuation is the more sensitive parameter.

When apparatuses such as those shown in FIGS. 1A, 2A, 4A, 5A, 6D or 7 are used sample and reference measurements are made as noted previously by cycling from a separating/concentrating/aggregating operational mode of high intensity to a measuring operational mode of one or more lower intensities. Cycling is effected over a short time duration typically 0.1 second wherein the temperature remains essentially constant. This time duration is to be compared to prior art acoustic measurement methods where one to two minutes are needed to make the measurements.

During the high intensity aggregating operational mode, the large particles are brought together and remain aggregated. This is followed by a low intensity measuring operational mode where the aggregates are still aggregated and a sample measurement is made. This is then followed, typically but without intending to be limiting, by an even lower intensity measuring operational mode, where the large particle aggregates disaggregate and an essentially isotropic distribution of the large particles is obtained. This isotropic distribution is measured and this measurement serves as the reference reading.

Typically, the low intensity measurement mode is effected first using intensities of about 0.01 W/cm$^2$ for a duration of 0.1 second. This measurement represents the reference measurement. Then the particles are aggregated for a period of 1-2 seconds using high acoustical intensities of from about 1 to about 30 W/cm², typically about 10 W/cm², and then the concentration of the sample is measured at a lower intensity of from about 0.5 to about 1 W/cm². This latter measurement which represents the sample measurement is also effected for a duration of 0.1 second.

As noted previously, the values determined for the change in $f_1$, $f_2$ and $\delta f_1$, $\delta f_2$ and their frequency dependences are then compared to calibrated values obtained using known concentrations and the sample's concentration is determined.

In addition to acoustical methods, the determination of concentration for large particles may be made by optical means using the apparatus described herein above with reference to FIG. 1A. Often both the acoustical and optical methods of the present invention are used to measure their respective parameters on the same sample. However, this is not mandatory and the optical method does not have to be used.

When using the digital camera of FIG. 1A, measurements are generally made at the center node 52 (as indicated in FIG. 3) of the resonance cavity. At center node 52 the large particles for which a concentration measurement is to be made have been concentrated by the standing waves in the resonator. Center node 52 lies at the node of one or more standing waves in the resonator. Similarly, the essentially particle free area between resonator center node 52 where the particles have been aggregated and circle 54 (FIG. 3) is also measured. This latter measurement serves as a reference. As shown in FIG. 3, particles are substantially absent within circle 54 except at center node 52.

Known concentrations of the large particles are measured using similar optical means under identical conditions. These serve as calibration values with which to compare and determine the concentration of the sample being measured.

When flow-through measurements are made using the apparatus of FIG. 1A, the large particles being measured are effectively concentrated at the standing wave nodes. After arriving at a value for the sample being measured at center node 52 of the resonator as discussed above, the value is adjusted by dividing it by the known total sample volume that has flowed through the apparatus.

While the above measurement uses a digital camera, other spectrometric instruments may be used. These include instruments which may be based on different types of radiation, that is infrared, visible and ultraviolet radiation or on different types of optical phenomena such as absorption, backscattering and fluorescence. As above, the results are compared to calibrated known concentrations to obtain the concentration of the sample.

While the means for determination of concentration has been described in terms of measuring acoustic and/or optical parameters this is not to be construed as limiting. As noted above, other physical or chemical parameters that can be correlated with concentration may also be used.

EXAMPLE

The following is an example of the separation of somatic cells and fat particles in milk using the apparatus and method of the present invention. Monitoring of the somatic cells and fat particles was made by measuring optical density and determining ultrasonic velocity.

The somatic cell count (SCC) and fat particle concentration of the milk sample was determined during milking using the following procedure. A milk sample was transmitted to the acoustic standing wave manipulating device and to the measuring chamber, i.e. the cavity of its cylindrical acoustic resonator.

Figure 8:
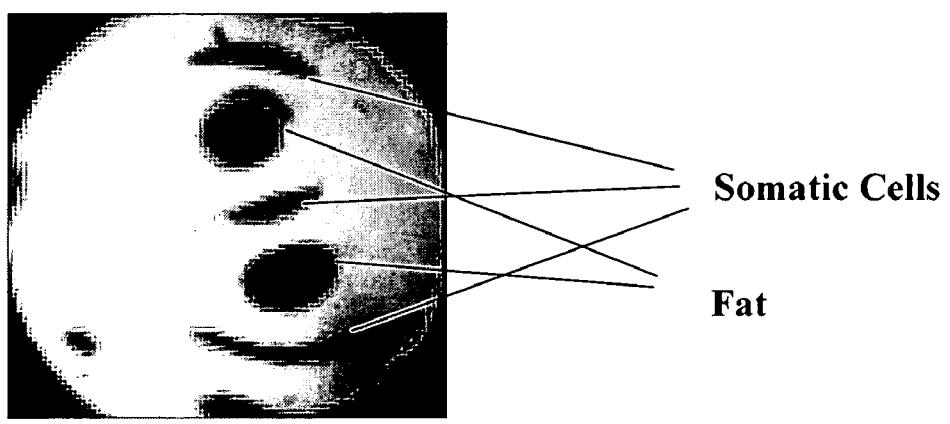
FIG. 8 shows the separation of fat particles and somatic cells in milk using the method and apparatus of the present invention.

FIG. 8 shows the separation of the fat and somatic cell portions using the apparatus of the present invention. The distribution is similar to that shown in and discussed above with FIG. 3.

The apparatus of the present invention was connected directly to the milking system. The milk sample was brought to 20° C. and its somatic cell and fat fractions were separated using a flow-through apparatus as in FIG. 1A. Every 2 sec. during a 30 sec. period, ultrasound attenuation, ultrasound velocity, and optical density were measured using the apparatus. The electronic signals were transmitted to a CPU and the concentration of the fat component and the somatic cell count were computed based on calibrated values. The milk components were also analyzed using the IR-Fosselectric method, well-known in the dairy industry, and the results obtained by the two methods were compared. The IR-Fosselectric method uses a Foss Milko-scan Milktester MK III apparatus based on IR measurements.

A comparison of the results of a milk sample analysis using the method and apparatus of the present invention and by the IR-Fosselectric method (denoted as reference) is shown in Table I.

The comparison indicates that the results using the method and apparatus of the present invention are accurate and close to results obtained using another widely used, commercially available method.

TABLE 1

| Fat (Method and apparatus of present invention) in mg/ml × 10 | Fat (Reference) in mg/ml × 10 | Difference (%) | Somatic Cells (Method and apparatus of present invention) in kilocells/ml | Somatic Cells (Reference) in kilocells/ml | Difference (%) |
| --- | --- | --- | --- | --- | --- |
| 3.36 | 3.38 | −0.59 | 220 | 231 | −4.76 |
| 2.08 | 2.02 | 2.97 | 344 | 334 | 2.99 |
| 4.01 | 4.04 | −0.74 | 118 | 125 | −5.60 |
| 3.56 | 3.58 | −0.56 | 128 | 121 | 5.79 |
| 2.33 | 2.37 | −1.69 | 532 | 555 | −4.14 |
| 4.44 | 4.4 | 0.91 | 176 | 151 | 16.56 |
| 5.47 | 5.49 | −0.36 | 137 | 120 | 14.17 |
| 4.36 | 4.34 | 0.46 | 149 | 143 | 4.20 |
| 2.53 | 2.57 | −1.56 | 112 | 119 | −5.88 |
| 3.71 | 3.76 | −1.33 | 131 | 135 | −2.96 |
| 3.81 | 3.89 | −2.06 | 106 | 116 | −8.62 |
| 2.14 | 2.11 | 1.42 | 725 | 690 | 5.07 |
| 5.67 | 5.69 | −0.35 | 344 | 362 | −4.97 |
| 3.47 | 3.43 | 1.17 | 136 | 147 | −7.48 |
| 3.89 | 3.85 | 1.04 | 125 | 113 | 10.62 |
| 2.65 | 2.69 | −1.49 | 130 | 138 | −5.80 |
| 4.36 | 4.33 | 0.69 | 143 | 128 | 11.72 |
| 3.35 | 3.32 | 0.90 | 102 | 109 | −6.42 |
| 2.23 | 2.28 | −2.19 | 74 | 82 | −9.76 |
| 4.55 | 4.42 | 2.94 | 202 | 220 | −8.18 |
| 5.01 | 5.07 | −1.18 | 173 | 178 | −2.81 |
| 3.46 | 3.44 | 0.58 | 142 | 149 | −4.70 |
| 2.8 | 2.83 | −1.06 | 421 | 399 | 5.51 |
| 4.12 | 4.1 | 0.49 | 155 | 176 | 11.93 |
| 3.66 | 3.61 | 1.39 | 123 | 132 | −6.82 |
| 2.77 | 2.76 | 0.36 | 99 | 112 | 11.61 |
| 4.17 | 4.19 | −0.48 | 138 | 120 | 15.00 |
| 2.47 | 2.45 | 0.82 | 149 | 131 | 13.74 |
| R | 0.998 | | | 0.989 | |
| STAND- | | 1.36 | | | 8.85 |

TABLE 1-continued

| Fat (Method and apparatus of present invention) in mg/ml × 10 | Fat (Reference) in mg/ml × 10 | Difference (%) | Somatic Cells (Method and apparatus of present invention) in kilocells/ml | Somatic Cells (Reference) in kilocells/ml | Difference (%) |
|---|---|---|---|---|---|
| ARD DEVIATION (in %) | | | | | |

In another embodiment of the apparatus, the connecting sleeves may be positioned so that the flow of fluid assists in aggregating the large particles. The placement of the connecting sleeves in FIG. 1A causes fluid to flow in a direction perpendicular to the movement of the particles resulting from the standing acoustic wave(s). In other embodiments, the connecting sleeves can be positioned so that fluid flows in a direction generally parallel to that of the particles under influence of the acoustic waves. The hydrodynamic forces then assist the primary and secondary acoustically generated forces (see discussion above with reference to FIG. 2C) to concentrate and/or aggregate the particles at the nodes of the standing wave (FIG. 2C) or solely at the wave's central node (FIG. 4C3).

In what has been discussed above, liquid multi-component systems have been described. However, it should be readily apparent to one skilled in the art that the method and apparatus described herein can be extended to gaseous systems such as aerosols. In particular, they can be applied to biologically hazardous aerosols, such as anthrax aerosols.

The method and apparatus described above can be used with biological systems which contain many different types of biological or biochemical species. In particular it is contemplated that the method and apparatus above may be used with epitopic capturing agents or liganding species deposited on heavier substrates. These substrates may include polymer substrates in the form of beads, such as polystyrene or polyacrylamide beads, latex beads and glass beads. The present method and apparatus can be used to separate the captured or liganded species and may also be used to determine the degree of association of the antibody-antigen complex.

All patents mentioned in this specification are herein incorporated in their entirety by reference into the specification, to the same extent as if each individual patent was specifically and individually indicated to be incorporated herein by reference. In addition, citation or identification of any patent or reference in this application shall not be construed as an admission that such patent or reference is prior art vis-a-vis the present invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for determining the concentration of a large particle component in a multi-component system, said method comprising the steps of: separating and concentrating by acoustic means the large particle component of the system, wherein the acoustic means generates at least one cylindrical standing wave in an acoustic cylindrical standing wave resonator; and measuring at least one acoustical parameter of the separated large particle component, thereby to determine its concentration with the sample and reference measurements required for the concentration determination made substantially concurrently in a single resonator cavity.

2. A method according to claim 1, wherein the at least one cylindrical standing wave is at least two cylindrical standing waves, each wave having a different frequency and intensity.

3. A method according to claim 1, wherein the at least one cylindrical standing wave is at least two cylindrical standing waves, each wave having a different frequency and the same intensity.

4. A method according to claim 1, wherein the large particles forming the large particle component being separated has a particle size within the range of from about 50 nanometers to about 500 microns.

5. A method according to claim 1, wherein said step of measuring at least one acoustical parameter further includes the step of measuring at least one optical parameter, the optical parameter selected from a group of optical parameters consisting of optical absorbance, fluorescence, and reflectance.

6. A method according to claim 5, wherein the optical parameter being measured in said step of measuring at least one optical parameter further includes the step of measuring the anisotropies of the at least one optical parameter.

7. A method according to claim 1, wherein in said step of measuring, the at least one acoustical parameter being measured is at least one acoustical parameter selected from a group of acoustical parameters consisting of acoustic wave velocity, acoustic wave attenuation, and acoustic impedance and wherein the at least one acoustical parameter is measured in two directions the directions being perpendicular to each other, with the measurement in one direction representing a reference measurement.

8. A method according to claim 1, wherein the at least one acoustical parameter in said step of measuring is measured at at least one low acoustic intensity ranging between about 0.01 to about 1 W/cm$^2$, while separation and concentration of the large particles in said step of separating is effected at high acoustic intensities ranging between about 1 to about 30 W/cm$^2$.

9. A method according to claim 8, wherein in said step of measuring a reference measurement is effected at a low acoustic intensity of about 0.01 to less than about 0.5 W/cm$^2$ and a sample measurement is effected at a low acoustic intensity of 0.5 to about 1 W/cm$^2$.

10. A method according to claim 1, wherein said method further comprises the step of comparing the measured value of the at least one acoustical parameter to values calibrated as a function of concentration.

11. A method according to claim 1, wherein the at least one cylindrical standing wave is at least two independent cylindrical standing waves, each wave having a different frequency and intensity.

12. A method according to claim 1, wherein the at least one cylindrical standing wave is at least two independent cylindrical standing waves, each wave having a different frequency and the same intensity.

13. An apparatus for determining the concentration of large particles in a multi-component fluid system, said apparatus comprised of:

an acoustic standing wave manipulating device, said device comprised of:
  a cylindrical acoustic standing wave resonator for containing a sample of the system; and
  at least one acoustic standing wave generating source disposed adjacent to and acoustically coupled to said resonator, said at least one generating source generating at least one acoustic standing wave for concentrating and aggregating the large particles at at least one nodal region of the wave, and
  wherein said cylindrical standing wave resonator includes at least one circumferential non-interference band near at least one end of said at least one acoustic standing wave generating source;
electronic circuitry for actuating and controlling said at least one acoustic standing wave generating source and the frequencies and acoustical intensities generated by said source; and
means for measuring at least one parameter of the sample after the large particles have been concentrated and aggregated by the at least one standing wave.

14. An apparatus according to claim 13, wherein each of said at least one non-interference bands is a circumferential bulge integrally formed in the walls of said cylindrical resonator or a circumferential constriction integrally formed in the walls of said cylindrical resonator.

15. An apparatus according to claim 14, wherein said cylindrical standing wave resonator is formed with a circumferential non-interference band near each end of each of said at least one acoustic standing wave generating sources.

16. An apparatus according to claim 15, wherein said at least one acoustic resonator is a plurality of acoustic resonators in fluid communication with each other, each resonator acoustically coupled to a different acoustic standing wave generating source, and each resonator having at least one non-interference band at each end of each of its generating sources.

17. An apparatus according to claim 16, wherein said plurality of acoustic resonators includes resonators of different volumes.

18. An apparatus according to claim 13, wherein said means for measuring is an acoustic means operative to measure at least one acoustical parameter, wherein said acoustic means is at least one piezoelectric transducer element.

19. An apparatus according to claim 18, wherein said means for measuring is an acoustic means and said apparatus additionally includes an optical means operative to measure at least one optical parameter, wherein said optical means includes at least one optical beam source and at least one optical beam detector.

20. An apparatus according to claim 13, wherein said cylindrical standing wave resonator is a cylinder acoustically coupled to said at least one acoustic standing wave generating source wherein said at least one acoustic standing wave generating source comprises at least one pair of piezoelectric transducer elements, each transducer element shaped as a segment of a cylinder.

21. An apparatus according to claim 13, wherein said at least one acoustic standing wave generating source is two generating sources, each disposed at 90° from the other, each source comprised of at least one piezoelectric transducer element.

22. An apparatus according to claim 13, wherein said electronic circuitry includes means to cycle through multiple frequencies with which to actuate said at least one acoustic generating source and thereby produce multiple cylindrical standing waves for concentrating and aggregating the large particles at the central node of the waves.

23. A method for determining the concentration of a large particle component in a multi-component system, said method comprising the steps of:
  separating and concentrating by acoustic means the large particle component of the system, wherein the acoustic means generates at least one cylindrical standing wave in an acoustic cylindrical standing wave resonator; and
  measuring at least one acoustical parameter of the separated large particle component, thereby to determine its concentration,
  wherein the at least one acoustical parameter in said step of measuring is measured at at least one low acoustic intensity ranging between about 0.01 to about 1 $W/cm^2$, while separation and concentration of the large particles in said step of separating is effected at high acoustic intensities ranging between about 1 to about 30 $W/cm^2$.

24. A method according to claim 23, wherein in said step of measuring a reference measurement is effected at a low acoustic intensity of about 0.01 to less than about 0.5 $W/cm^2$ and a sample measurement is effected at a low acoustic intensity of 0.5 to about 1 $W/cm^2$.

* * * * *